INTERMEDIATES FOR POLYCYCLIC QUINONOID ANTIBIOTICS

RELATED APPLICATIONS

This is a division of application Ser. No. 632,939, filed Nov. 18, 1975, now U.S. Pat. No. 4,070,382.

BACKGROUND OF THE INVENTION

Adriamycin, an antibiotic compound which is usefull in the treatment of certain tumors is described and claimed in U.S. Pat. No. 3,590,028, to Arcamone, et al. A further procedure for the preparation of adriamycin will be found in U.S. Pat. No. 3,803,124 to Arcamone, et al. Said patent also discloses that the adriamycin may be prepared from daunomycine or its aglycone daunomycinone which are described and claimed in U.S. application Ser. No. 404,550, filed Oct. 6, 1964, by D. I. Marco, et al.

A total synthesis of daunomycinone has been disclosed by Wong, et al, (Canad. J. Chem., 51, 446 (1973)). This synthesis, while apparently operative, gives such small yields that its use as a commercially viable alternative to the fermentation derivation of daunomycin and adriamycin is not considered feasible.

A further approach to the synthesis of (+)-9-deoxydaunomycinone, another intermediate in the synthesis of daunomycin, is disclosed by the Applicant herein and coworkers in J. Amer. Chem. Soc., 97, 4425 (1975). This approach is quite different from the approach to the synthesis of daunomycinone to be described and claimed herein.

It should also be noted that the coupling of daunomycinone with the appropriate sugar to yield daunomycin (also known as daunorubicin) is found in Acton, et al., J. Med. Chem., 17, 659, (1974). The sugar, daunosamine utilized in the Acton synthesis of daunomycinone is disclosed in Marsh, et al, Chem. Commun., 973, (1967).

DESCRIPTION OF THE PRIOR ART

The first novel compound in the synthetic sequence to be disclosed and claimed herein is the ether of 5-hydroxy-quinizarinquinone, in particular, the lower alkyl, especially the methyl ether thereof. The immediate precursor in the present synthesis is 1,4,5-trimethoxy-9,10-anthraquinone which is described in several publications, for example, Wiles and Thomas, J. Chem. Soc., 4811 (1956). The 5-hydroxy-1,4,9,10-anthradiquinone is also known. (Dimroth and Hilcken, Ber., 54, 3050 (1921)). While it might be thought, that the 5-hydroxy anthradiquinone is a suitable starting material for the corresponding ether, that is, in fact, not the case. It is taught by Wiles and by Dimroth that the conditions which would be required to alkylate, in particular, methylate a hydrogen bonded phenol of this type would be so vigorous as to destroy the desired product. It should be noted in this connection that the 5-methoxy ether decomposes above 85° C. or in the presence of a strong base, and thus would not be readily accessible by the O-alkylation, suitably methylation of the corresponding phenol.

The oxidative dealkylation of the triether of 1,4,5-trihydroxy-9,10-anthraquinone to the corresponding monoether of 5-hydroxy-1,4,9,10-anthradiquinone is accomplished by the method of Snyder and Rappaport, J. Amer. Chem. Soc., 94, 227 (1972).

A Diels-Alder reaction of a type related to, but distinguishable from, the conversion of the quinizarinquinone (III) in the principal reaction sequence to the corresponding naphthacenetetraone (IV) is disclosed in Inhoffen, et. al, Ber. 90, 1448 (1957). The present reaction can be distinguished therefrom in that the reaction of the reference is concerned with esters and ethers of 1-hydroxy-1,3-butadiene and the present reaction sequence is concerned with esters of 2-hydroxy-1,3-butadiene. While this difference may appear, at first glance, to be minor, it should be noted that the reference is concerned not only with addition at the 2 and 3 positions but also at the 4a and 9a positions of the quinizarinquinone nucleus. The provision of the good yields obtained in the present process by addition across the 2 and 3 positions cannot be considered to be a foregone conclusion and is highly dependent on the substituent(s) in the diene component. Thus, 2-ethoxy-1,3-butadiene in our hands adds mainly to the undesired 4a,9a double bond, as do certain Examples cited by Inhoffen.

SUMMARY OF THE INVENTION

There is provided a novel process for the preparation of certain polycyclic quinones and polyquinones, in particular, there is provided a method of synthesizing (+)-daunomycinone and analogs thereof.

The general reaction scheme is set forth herein below. It should be noted that compound I wherein $R_1$ equals $R_2$ equals $R_3$ equals methyl is a known compound. Similarly, compound II wherein $R_1$ equals $R_2$ equals $R_3$ equals methyl or H are known compounds.

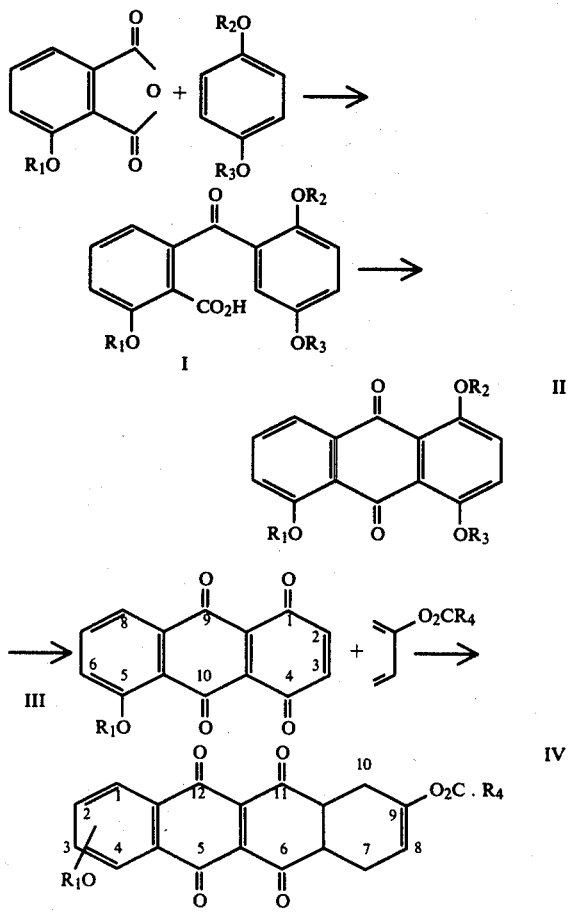

United States Patent [19]

Kende et al.

[11] 4,147,706
[45] Apr. 3, 1979

[54] INTERMEDIATES FOR POLYCYCLIC QUINONOID ANTIBIOTICS

[75] Inventors: Andrew S. Kende, Pittsford; John E. Mills, Rochester, both of N.Y.; Yuh-Geng Tsay, Taichung, Taiwan

[73] Assignee: Research Corporation, New York, N.Y.

[21] Appl. No.: 868,373

[22] Filed: Jan. 10, 1978

Related U.S. Application Data

[62] Division of Ser. No. 632,939, Nov. 18, 1975, Pat. No. 4,070,382.

[51] Int. Cl.$^2$ .............................................. C07C 87/10
[52] U.S. Cl. .................................... 260/365; 260/376; 260/383; 424/331; 424/340
[58] Field of Search ....................... 260/365, 376, 383

[56] References Cited

U.S. PATENT DOCUMENTS

| | | | |
|---|---|---|---|
| 3,686,163 | 8/1972 | Arcamone et al. | 260/383 X |
| 3,803,124 | 4/1974 | Arcamone et al. | 260/365 X |
| 3,963,760 | 6/1976 | Bernardi et al. | 260/365 |
| 3,987,028 | 10/1976 | Lunel et al. | 260/365 X |
| 4,070,382 | 1/1978 | Kende et al. | 260/365 |
| 4,077,988 | 3/1978 | Arcamone et al. | 260/376 |

*Primary Examiner*—Paul F. Shaver
*Attorney, Agent, or Firm*—Omri M. Behr

[57] ABSTRACT

There is provided a novel method of synthesizing certain tetracyclic quinones. In particular, there is provided a novel route to the synthesis of (+)-7-deoxydaunomycinone and analogs thereof, which includes the provision of novel tri- and tetracyclic quinone intermediates. The -7-deoxydaunomycinone derived from naturally occurring daunomycin is a known compound, which is itself an intermediate in the preparation of the clinically accepted anti-tumor antibiotics daunomycine and its derivative adriamycin.

19 Claims, No Drawings the 7-hydroxyl may be accomplished by a novel variant of benzylic bromination followed by solvolysis. The subsequent glycosidation at the C-7 hydroxyl is achieved in the manner set forth hereinabove by Acton, et al.

DESCRIPTION OF THE PREFERRED EMBODIMENTS

Preparation of Starting Materials

The starting materials of the process of the present invention may be considered the compounds of formula (III) hereinabove. The 4-hydroxyquinizarinquinone of this general formula is a known compound and may be prepared either by the method of Dimroth and Hilcken (Ber., 54, 3050 (1921), or Kirk, et al, (U.S. Pat. No. 1,963,136). Where compound (III) is a 4-ether it is to be considered a novel compound and may be prepared by generally known methods from the appropriate ether of 3-hydroxyphthalic anhydride. In this procedure, there may be employed an appropriate ether, for example, the ether group may be alkyl, suitably lower alkyl, for example, methyl, ethyl, propyl, butyl, or pentyl. The ether may also be an aralkyl ether such as a phenyl-alkyl or substituted phenyl-alkyl ether, suitably where the alkyl is a lower alkyl, for example, wherein lower alkyl is as listed above and the substituents of which there may be between 1 and 5, and may be alkyl, suitably lower alkyl, such as those listed above, or alkoxy, suitably lower alkoxy such as the oxy derivatives of the lower alkyl moieties listed above, or halo, for example, fluoro, chloro, bromo or iodo. Furthermore, hereinabove and hereinbelow the prefix "lower alk" shall be considered as designating a saturated carbon skeleton bearing hydrogen atoms on said skeleton in all positions except where said skeleton is bonded to another group and containing 1-5 carbon atoms.

Where compound III is a 4-ester, it can be prepared from the appropriate ester of 3-hydroxyphthalic anhydride in the same manner as the 4-ether.

The phthalic anhydride is then subjected to a Friedel-Crafts reaction with hydroquinone, hydroquinone diether or hydroquinone diester. The ether groups utilized may be the same as each other or different from each other and may be the same as or different from the ether moiety on the 3-position of the phthalic anhydride with which it is to be reacted. Since however in a subsequent stage of this reaction, said ether groups are to be oxidatively removed to form a quinone moiety, it is preferred to utilize any readily available ether in this category of which p-dimethoxybenzene is preferred. In carrying out the Friedel-Crafts reaction, the 3-hydroxyphthalic anhydride or its derivatives is taken up in a dry reaction inert organic solvent to form a solution or suspension therein. The solvent utilized should of course be non-hydroxylic; solvents such as methylene chloride, nitrobenzene or carbon disulfide are considered suitable. To the mixture is added an excess, suitably about 100% excess of anhydrous aluminum chloride. There is no specific temperature limitation upon the reaction, however, the reaction is rather slow at temperatures below 0° C., and proceeds too rapidly at elevated temperatures, thus it has been found advantageous to carry out the reaction at ambient temperatures, that is to say, at temperatures between about 10° and about 30° C., suitably about 20° C. To this solution is added the hydroquinone derivative in a similar solvent. There is utilized an excess of said hydroquinone derivative, suitably a 100% excess relative to the anhydride.

The reaction mixture is stirred vigorously and after completion of the addition agitation is continued at ambient temperature for from about 12 to 36 hours.

The reaction is then quenched by pouring it onto a mixture of ice and concentrated hydrochloric acid. The slurry is agitated vigorously and then extracted with a water immiscible polar organic solvent, suitably a halogenated hydrocarbon solvent such as chloroform. Other organic solvents, for example, hydrocarbon solvents such as benzene, may be employed but are not preferred. During this extraction some of the desired ketoacid may precipitate and is collected by filtration.

The organic extract is washed with water, extracted with mild aqueous base, suitably saturated alkali metal carbonate or bicarbonate, such as sodium carbonate or bicarbonate, and said aqueous basic extract after washing with a fresh sample of the organic solvent used in the previous step, is acidified, suitably with a mineral acid, preferably with concentrated hydrochloric acid, cooled, suitably to between −5 and +5° C. and the precipitate thereby formed is separated, preferably by filtration. There is thus obtained a product of general formula (I) in the foregoing flow chart which, except for the desired step of drying same to remove the moisture therefrom, is of sufficient purity for use in the next step of the reaction.

Compound (I) is then converted to the corresponding anthraquinone (II) by reaction with a cyclodehydrating agent. Any reagent which will thus dehydrate an O-benzoylbenzoic acid may be utilized. Among these reagents may be listed phosphorus pentoxide, polyphosphoric acid, anhydrous hydrogen fluoride and concentrated sulphuric acid; of these concentrated sulphuric acid is to be preferred. Compound (I) is added portionwise to a substantial excess of agitated concentrated sulphuric acid. After addition is complete the mixture is heated to moderately elevated temperatures suitably from about 70° to about 90° C., with constant agitation, for from about 15 to about 40, suitably from about 20 minutes. The now blue-colored mixture is cooled to ambient temperature and then the reaction is quenched by pouring onto crushed ice. The aqueous mixture is then extracted with a water immiscible organic solvent, preferably a polar organic solvent, suitably a halogenated hydrocarbon solvent, preferably chloroform, and the organic extract washed with dilute aqueous alkali, and the water, following which the extract is dried and the solvent removed to yield the desired product (II). It is preferred to further purify compound (II) and such purification may be achieved by recrystallization, suitably from a lower alkanol, such as ethanol or 2-butanol.

Compound (II) is then oxidized to Compound (III). In the case of triether, Compound (II) is taken up in a reaction inert, water-miscible organic solvent. In view of the fact that the present step involves oxidation, said solvent should be relatively inert to oxidation. It has been found that ketones, suitably dialkyl ketones, preferably acetone, may be utilized. It is further preferred that the solvent be heated to a temperature at or near its boiling point.

To the warm solution is added a substantial excess of the oxidizing agent. It is preferred to utilize between 2 to 6 moles, suitably about 3 to about 5 moles of oxidizing agent per mole of compound (II). It has been found advisable to briefly sonicate the mixture to obtain uniform dispersal of the oxidant. Among the oxidizing agents which may be used silver (II) oxide (argentic oxide) is especially preferred. The mixture is then heated, suitably under reflux, and vigorously agitated. The reaction is then initiated by the addition of a small amount of acid, suitably mineral acid, preferably concentrated nitric acid. The reaction is rapid and should be considered complete in 10–30 minutes.

The acid utilized should be a strong acid, however, the quantity thereof is more critical than its nature. The amount of acid utilized should be just sufficient to dissolve all of the silver oxide. If an amount substantially greater than this is employed, the water present in the acid will interfere with reaction and lower the yields obtained. The reaction mixture is then filtered, and the residue washed thoroughly with water and dried under reduced pressure to yield the appropriate 4-ether compound (III) in sufficient purity to take part in the next stage of the reaction.

Where Compound (II) carries ester groups in the 1 and 4 position (i.e. $R_2$ and $R_3$ are acyl as defined) the compound is cleaved to yield the free hydroquinone analog.

Where compound (II) has a hydroquinone structure ($R_2 = R_3 = H$) oxidation to III is preferably accomplished using lead tetraacetate in acetic acid.

The 4-hydroxyquinizarinquinone or 4-ether thereof (Compound III) is taken up in an organic solvent, preferably in the presence of an organic acid and subjected to a Diels-Alder condensation with 2-hydroxy-1,3-butadiene 2-ester. Since the ester group at the 2 position of the butadiene will be removed in the next but one stage of the reaction sequence, the nature thereof is in no way critical. Any fairly readily hydrolyzable ester group may be employed. These include alkanoates, suitably lower alkanoates such as acetate, propionate, butyrate, valerate, and the like, aroyl esters for example benzoate and naphthoate, and their nuclearly substituted derivatives, aralkanoates, suitably aryl lower alkanoates, such as phenyl lower alkanoates, suitably benzylacetate, benzylpropionate, benzylbutyrate, and the like. Among these groups the acetate and the benzoate are to be preferred merely for reasons of ready accessibility and cost.

The reaction may be carried out in polar or nonpolar solvents, hydrocarbon solvents, suitably aromatic hydrocarbon solvents such as xylene or toluene may be employed, similarly halogenated hydrocarbons such as chloroform or methylene chloride may be used, equally mixtures of both of these groups of solvents may be employed. To improve the yield of the desired adduct it has been found advantageous to employ an organic acid as solvent or cosolvent. It has been found that lower alkanoic acids suitably acetic acid are to be preferred. It has been found suitable to prepare a solution of between 5 and 15% by weight of the reactants in a solvent mixture of the inert solvent and the acid. A mixture of 1 part of solvent to 2 parts (by volume) of the acid have been found suitable, although pure acetic acid is also satisfactory. In order to maximize the yield of desired product, that is to say, a compound wherein the addition takes place as shown in compound IV, rather than at the 4a and 9a positions, the reaction should be carried out under the mildest conditions concomitant with reasonable reaction rates. Thus, it is preferred to run the reaction at ambient temperature, that is to say, between about 10° and about 40° C., suitably about 20° C. for from about 2 to about 6 days under agitation, at about 20° C. the time for completion of the reaction is about 4 days. The adduct (IV) formed in the reaction usually separates cut as a precipitate and may be removed from the reaction mixture by filtration. The adduct may then be purified, suitably by washing with water and drying under reduced pressure.

The adduct (IV) is then enolized to the phenolic tautomer (V). The enolization is achieved by treatment of IV with a proton acceptor or proton donor in a suitable organic solvent. It has been found that salts of alkanoic, aroic or aralkanoic acid, such as acetates, butyrates, benzoates, naphthoates, phenyl acetates, phenyl propionates, and the like in the presence of the corresponding acid, suitably the same acid as that forming the anion of the salt, may be employed. The preferred conditions include, for example warming the compound in an alkanoic acid solvent containing either an alkali salt of that acid, or mineral acid, or p-toluene sulfonic acid. In the preferred variant of the reaction, the adduct is dissolved in glacial acetic acid at a temperature just below its boiling point, and the proton acceptor, preferably anhydrous sodium acetate, added thereto. There need only be utilized between 0.1 and 0.3 mg of the proton acceptor per mole of adduct. The enolization takes place very rapidly, but it is desirable to continue heating for 1 or 2 minutes after the addition. The reaction mixture is then cooled to ambient temperature, sufficient water added to precipitate the enolized adduct which is then separated suitably by filtration, washed, and dried under reduced pressure.

The two-step conversion of Diels-Alder adducts (IV) to the corresponding 9-ketones (VI) can be combined into one by warming compounds (IV) with a small amount of strong acid in a water-miscible organic solvent (e.g. lower alcohols), followed by work-up as described above for (VI). This alternative route proceeds in yields similar to the two-step sequence.

The enol ester (V) is then hydrolyzed to the corresponding 9-ketone (VI). While the hydrolysis itself is a step which is well known in the art, extreme care must be taken that in the course of this step the presence of oxidizing agents, in particular, air, are held to an absolute minimum in order to avoid unwanted aromatization of the saturated alicyclic ring. This aim is suitably achieved by degassing the reaction medium and carrying out the reaction in the presence of a substantially inert gas. For this purpose any of the inert gases or nitrogen may be utilized, nitrogen being preferred for reasons of cost. In the preferred procedure, the enol ester (V) is suspended in an alkanol, suitably a lower alkanol, for example, ethanol, the suspension degassed and the container flushed with nitrogen. There is added to the suspension, an excess of mineral acid, preferably 6N hydrochloric acid, since this acid does not have any oxidizing properties. Degassing and nitrogen flushing procedure is again repeated, the mixture heated under reflux for from about 4 to about 8 hours, suitably for about 6 hours, cooled to ambient temperature, suitably about 20° C., diluted with water and the aqueous mixture extracted with a suitable immiscible organic solvent, preferably halogenated hydrocarbon solvent, such as chloroform. The chloroform extract is washed with water, dried, and the solvent removed to leave a residue which is then purified to yield the desired 9-ketone (VI) which is then purified.

Purification of the 9-ketone may be carried out by chromatography. Where small quantities are involved, chromatography on silica gel plates and elution with 5% hexane in chloroform or 3% methanol in methylene chloride has been found operative. It should be noted that the product (VI) is not a single compound but is in fact the regioisomeric mixture of the 1- and 4-ethers or phenols as the case may be. In some reactions the 9-ketone precipitates directly from the aqueous-ethanolic reaction mixture enriched in the 4-methoxy regioisomer.

These regioisomers may be separated by differential crystallization. It has been found very useful to carry out this crystallization in ethanol. The 4-isomer is the less soluble and may be readily separated from the 1-isomer by treatment with boiling ethanol followed by filtration. It has been found sufficient to carry out two (2) treatments in this manner, in order to remove the 1-isomer from the 4-isomer. Needless to say, there will be a certain loss of 4-isomer in the solution thus removed, however, this may be recovered by crystallization techniques well known in the art. Other solvents such as ethyl acetate or isoamyl alcohol may also be employed for the separation but offer no advantage.

While it is preferred to carry out the aforementioned resolution of the regioisomers prior to the ethynylation step, the reactions are operative without said step and the resolution may be carried out at a later stage. Hence, any statements which are made hereinbelow with respect to the 4-hydroxy compound or the 4-ether are equally applicable to the mixture of the corresponding 1- and 4- regioisomers.

It is noteworthy that treatment of the 1- and 4-methyl ethers corresponding to strucutre VI ($R_1 = CH_3$) with anhydrous aluminum chloride in methylene chloride gives a high yield of the corresponding 1- and 4-hydroxy derivatives (VI) ($R_1 = H$), providing an alternative route to the latter compounds.

The ethynylation of compound (VII) may be carried out by reaction with an ethynyl Grignard reagent. In the preferred approach, acetylene is purified, suitably by passage thru, sequentially, alumina and concentrated sulphuric acid, and bubbled into a suitable ethereal solvent until said solvent is saturated with a sufficient quantity of acetylene, but bubbling is continued. Dioxan, tetrahydrofuran or diethylether may be employed, however, freshly distilled tetrahydrofuran under an inert atmosphere such as an nitrogen atmosphere is preferred. The acetylenic solution is then converted into the corresponding Grignard reagent in the usual manner, that is to say, a predetermined quantity of a suitable alkyl Grignard reagent, preferably a lower alkyl magnesium halide, most suitably ethyl magnesium halide, in an ethereal solution, is added in portions. When all of the said Grignard reagent has been added, the passage of acetylene is stopped and less than equimolar amount of a solution of compound (VI), preferably comprising about 0.01–0.2 moles relative to the Grignard reagent as prepared above, is added in a suitable ethereal solvent, preferably in dry tetrahydrofuran. The mixture is then agitated, suitably at ambient temperature, under an inert atmosphere, for from about 12 to about 18 hours. The reaction mixture is then quenched, preferably by the addition of cold saturated ammonium chloride solution, or aqueous oxalic acid, the organic (ethereal) phase set aside and retained, and the aqueous phase extracted with a suitable nonhydroxylic, water immiscible, organic solvent, preferably ethyl acetate. The ethyl acetate extract and the ether extract are then combined, dried, and evaporated to dryness to yield the ethynyl carbinol (VIII). This residue may be further purified.

The manner of purification is not critical and will depend upon the quantities available. It has been found found that chromatography on silica, utilizing as an eluent a mixture of an alkanol with an alkylene halide, suitably 3% methanol in methylene chloride may be employed.

The thus produced ethynyl carbinol (VIII) is then hydrated to form the desired 9-hydroxy-9-acetyl compound (IX). Where the substituent in the 4-position is methoxy, this compound will be ($\pm$)-7-deoxydaunomycinone and where the substituent at position 4 is hydroxy, the compound thus produced will be ($\pm$)-7-deoxycarminomycinone.

In this procedure the ethynyl carbinol (VIII) is taken up in a reaction-inert polar organic solvent, suitably a halogenated hydrocarbon such as chloroform, methylene chloride, or the like. There is also prepared a fresh solution of mercuric ion, preferably in the presence of a mineral acid. The source of the mercuric ion is not critical, salts of mineral acids such as mercuric sulphate or salts of organic acids, such as mercuric acetate or the yellow mercuric oxide itself, may be employed. It is generally preferred to utilize yellow mercuric oxide in a small amount of water containing about 15% per volume of concentrated sulphuric acid. The acidic solution is warmed to between 60° and 80° C., the solution of the carbinol added thereto, and the mixture heated, suitably under reflux, for from about 2 to about 6, suitably from about 4 hours, cooled to ambient temperature, quenched in water, and extracted with a suitable solvent, for example, a water immiscible organic solvent such as chloroform or the like. The organic extracts are washed, treated with a mild base, suitably saturated sodium bicarbonate, to remove residual traces of acid, dried and the solvent removed.

The residual material, compound (IX), may be then further purified, suitably by chromatography, preferably on silica gel, to yield the racemic mixture of the desired product.

In an alternative procedure, compounds (VIII) may be converted to the 9-acetates or trifluoroacetates of compounds (IX) by stirring with mercuric acetate or trifluoroacetate respectively in an inert polar organic solvent, preferably ethyl acetate. Under these reaction conditions, certain compounds of type VIII lead directly or in part to the free 9-hydroxy compounds (IX), isolated as noted above. Subsequent treatment of the 9-esters by dilute aqueous base yields the free 9-hydroxy compounds (IX), isolated and purified as described above.

As stated above, the compounds of general formula (IX) wherein the 4-substituent is methoxy, namely the ($\pm$)-7-deoxydaunomycinone, and where it is hydroxy, namely ($\pm$)-7-deoxycarminomycinone, may be converted to the 7-hydroxylated compounds by a sequence proceeding through benzylic bromination.

Although similar chemistry utilizing N-bromosuccinimide on related but different substrates has been reported by Wong, et al., (Canad. J. Chem., 51, 446, (1973)), that reagent is generally unsatisfactory when applied to the intermediates of our invention.

Compound (IX) (either as the mexiture of regioisomers or the 4-ether or hydroxy isomer) is treated with a free radical source of bromine under conditions which substantially reduce the accumulation of hydrobromine acid.

Suitably, compound (IX) is taken up in an inert, nonpolar organic solvent. Bromine, a similar solvent, is added in the presence of a free radical source, suitably a source of ultra violet light. The concentration of hydrobromic acid is reduced to preclude conditions of ionic bromination, a stream of inert gas, suitably a stream of nitrogen is passed continuously thru the reaction system. Other means of elimination of the acid may also be employed. Specifically, dry nitrogen is bubbled through a dilute solution of (±)-7-deoxydaunomycinone in carbon tetrachloride. The solution is irradiated with a sunlamp while a dilute solution of bromine in carbon tetrachloride is added (in large excess, say from 2–6 fold excess) over several, say, 1–4 hours under steady nitrogen bubbling and stirring. The brominated material is not isolated as such but is merely concentrated. The brominated material is then hydrolyzed to replace the bromine at the 7-position with a hydroxyl. The hydrolysis may be one stage or two stage.

In the single stage method, there is used water, mild base, such as aqueous alkali, an alkaline earth metal carbonate, such as sodium carbonate or calcium carbonate. Hydrolysis may be achieved in substantially non-aqueous media by passing a solution of the brominated material in an organic solvent over alumina or silica gel. While the reaction is carried out in a substantially dry environment — since otherwise the alumina on the silica gel would clog, it is advisable for either the solvent or, the alumina or the silica gel to contain some water, up to 10% by weight is suitable. Preferably, the residue taken up in chloroform, and the chloroform solution run through silica, either in the form of silica gel column or a silica gel plate. Elution with a suitable solvent, for example, 3% methanol in methylene chloride, yields a mixture of daunomycinone, epi 7-epidaunomycinone, and recovered starting materials in an approximate ratio of 2:3:1.5.

In the two-stage hydrolysis, the brominated material is treated with a suitable derivative of an alkanoic acid, an ester or the silver salt of an alkaline acid may be employed, suitably the silver salt is used. Most suitably, silver trifluoroacetate is employed. The thus produced 7-trifluoroacetate is readily removed, suitably with mild base to yield the desired 7-hydroxy derivative.

The epidaunomycinone may be readily converted to the desired daunomycinone by acid epimerization. In this procedure the epidaunomycinone is taken up in trifluoroacetic acid, allowed to stand at ambient temperature from about 1 to about 3 hours, quenched in water, extracted with a water immiscible polar non-hydroxylic solvent, preferably halogenated hydrocarbon solvent, such as chloroform, the solution washed with water, dried, and chromatographed as set forth above, to yield the desired daunomycinone in approximately 75% yield.

An entirely parallel sequence of benzylic bromination, solvolysis and acid-catalyzed 7-epimerization is carried out with (±)-7-deoxycarminomycinone to give (±)-carminomycinone.

An alternative route to (±)-7-deoxycarminomycinone may be achieved by O-demethylation of (±)-7-deoxydaunomycinone by anhydrous aluminum chloride in an inert organic solvent such as benzene or methylene chloride at temperatures of 10°–35°, preferably 20°, for about 16 hours. Under the same conditions, (±)-daunomycinone itself is O-demethylated to give (±)-carminomycinone in good yield; the natural (±)-daunomycinone reacts in the same manner to give (±)-carminomycinone. These procedures illustrate that synthetic access to the carminomycinone series is available either by starting with the 5-hydroxy variants of diquinone (III) or by demethylation of the above tetracyclic daunomycinone derivatives, or of the 4-methyl ether (VII) ($R_1 = CH_3$).

The synthetic (±)-7-deoxydaunomycinone prepared by this invention serves not merely as a precursor for useful anti-tumor substances, but also as a new and sensitive reagnet for certain metal ions, including cobalt (II), nickel (II), copper (II), and zirconium (IV). In the presence of the above divalent ions, a dilute (0.02–0.04 M) solution of (±)-daunomycinone in methanol was colored purple, and with zirconium (IV) a salmon pink color developed. The limit of detection by eye for cobalt (II) was $3 \times 10^{-8}$ M.

Optical resolution of synthetic (±)-daunomycinone is carried out by the conventional method of conversion to diastereomeric derivatives using a chiral resolving agent (Ct. Eliel, "Stereochemistry of Carbon Compounds", McGraw Hill, 1962, Chapter 4). In the preferred variant, (±)-daunomycinone is monoesterified with l-menthoxy acetyl chloride in pyridine, the diastereomeric C-7 esters separated by careful chromatography, and the ester derived from the (±)-daunomycinone cleared with dilute base to give (±)-daunomycinone.

The daunomycinone and the analogs thereof may be converted to the corresponding glycosides by methods well known and disclosed in the art.

EXAMPLE 1

2-(2′,5′-Dimethoxybenzoyl)-6-methoxybenzoic acid (I)

3-Methoxyphthalic anhydride (17.8 g, 0.1 mole) was suspended in 100 ml. dry methylene chloride (previously distilled over anhydrous potassium carbonate). To the suspension was added anhydrous aluminum chloride (30.5 g, 0.23 mole) in one portion. The suspension quickly became bright yellow and was stirred at room temperature for 2 hours. A solution of p-dimethoxybenzene (27.6 g, 0.2 mole) in methylene chloride (100 ml) was added slowly to the vigorously stirred solution. The reaction mixture was stirred overnight at 25° and poured onto ice (300 g) and concentrated hydrochloric acid (50 ml). The slurry was stirred for 30 minutes and extracted with chloroform (4 × 150 ml). A white precipitate suspended in the aqueous layer is collected by filtration. The organic extract was washed once with water (200 ml) and washed with saturated sodium bicarbonate (4 × 150 ml). The aqueous bicarbonate extract was washed once with chloroform (150 ml) and acidified with concentrated hydrochloric acid, the mixture cooled on an ice bath and filtered. The residue was washed well with water and dried under reduced pressure and combined with the white precipitate to yield 2-(2′,5′-dimethoxybenzoyl)-6-methoxybenzoic acid (I) as a pale yellow solid (13 g, 41% yield), m.p. 180°–182° C. (from ethanol); IR (KBr) 2.95, 5.72μ; NMR (CDCl₃) δ, 7.60–6.80 (m, 6H), 6.10 (s, 1H), 3.75 (s, 3H), 3.70 (s, 3H), 3.49 (s, 3H).

In accordance with the foregoing procedures, but where in place of p-dimethoxybenzene, there is used hydroquinone, there is obtained the corresponding 2-(2′,5′-dihydroxybenzoyl)-6-methoxybenzoic acid.

In accordance with the foregoing procedures, but where in place of 3-methoxyphthalic anhydride, there is utilized 3-acetoxy, or 3-benzoyloxyphthalic anhydride, there are obtained the corresponding 2-(2′,5′-dimethoxybenzoyl)-6-acetoxy, and 6-benzoyloxybenzoic acids.

In accordance with the immediately foregoing alternate procedure where in place of p-dimethoxybenzene there is utilized hydroquinone, there are obtained the corresponding 2-(2',5'-dihydroxybenzoyl)-6-acetoxy, and 6-benzoyloxy benzoic acids.

EXAMPLE II

1,4,5-Trimethoxyanthraquinone (II)

2-(2',5'-Dimethoxybenzoyl)-6-methoxybenzoic acid (I) (3 g, 0.01 mole) was added in portions to stirred concentrated sulfuric acid (20 ml). After addition the mixture was heated on steam bath with constant stirring for 20 minutes, cooled to room temperature and poured onto crushed ice (400 g) and extracted with chloroform (3 × 100 ml). The organic extract was washed with 2% aqueous sodium hydroxide solution (10 × 100 ml) and water (100 ml), then dried over anhydrous sodium sulfate and the solvent stripped off under reduced pressure to yield 1,4,5-trimethoxyanthraquinone (II), as a brownish yellow solid (2.7 g, 90% yield). Recrystallization from ethanol gave yellow crystals, m.p. 201°–203° C.; IR (CDCl$_3$), 5.92$\mu$; NMR (CDCl$_3$) $\delta$, 7.88–7.20 (m, 5H), 3.94 (s, 3H), 3.92 (d, 6H). Calcd: C, 68.46; H, 4-70. Found: C, 68.33; H, 4.82.

In accordance with the above procedures, but starting with any of the other benzoic acids prepared in accordance with Example I, there are obtained 1,4-dihydroxy-5-methoxyanthraquinone, 5-acetoxy-1,4-dimethoxyanthraquinone, 5-benzoyloxy-1,4-dimethoxyanthraquinone, 5-acetoxy-1,4-dihydroxyanthraquinone, and 5-benzoyloxy-1,4-dihydroxyanthraquinone respectively.

EXAMPLE III

5-Methoxyquinizarinquinone (III)

1,4,5-Trimethoxyanthraquinone (II) (0.596 g, 2 mmole) was dissolved in hot acetone (60 ml) and argentic oxide (1 g, 8 mmole) was added to this warm solution. Brief sonication formed a uniform dispersal of oxidant. The mixture was heated up to boiling on steam bath again and the mixture stirred vigorously with magnetic stirrer. The oxidation was then initiated by the addition of 6N aqueous nitric acid (2 ml). After addition, the mixture was stirred while cooling for an extra 20 minutes and filtered. The residue was washed thoroughly with water and dried under reduced pressure to give 5-methoxyquinizarinquinone (III) as a brownish yellow solid, (0.44 g, 82% yield). m.p. 252°–3° C. (decomp.); IR (KBr), 5.94, 6.05$\mu$; NMR (CDCl$_3$) $\delta$, 7.80–7.20 (m, 3H), 6.84 (s, 2H), 3.96 (s, 3H). Calcd: C, 67.1; H, 2.98. Found: C, 66.4; H, 2.92.

In accordance with the above procedure, but where in place of 1,4,5-trimethoxyanthraquinone there is utilized 5-acetoxy-1,4-dimethoxyanthraquinone or 5-benzoyloxy-1,4-dimethoxyanthraquinone, there is obtained the corresponding 5-acetoxyquinizarinquinone or 5-benzoyloxyquinizarinquinone.

EXAMPLE IV

5-Methoxyquinazirinquinone (III)

A mixture of 1,4-dihydroxy-5-methoxyanthraquinone (80 mg, 0.3 mmole), lead tetraacetate (180 mg, 10% acetic acid) and acetic acid (0.3 ml) was ground together in a 5 ml. flask for 10 minutes at 25°. The reaction mixture was filtered and the solid washed with water. The crude solid was taken up in a large volume of acetone, the solution filtered through Celite, dried over sodium sulfate and evaporated under reduced pressure to give 5-methoxyquinizarinquinone (48 mg, 60% yield). The spectra and mp of this diquinone were identical with those of the sample synthesized by the method of Example III.

In accordance with the above procedure but where in place of 1,4-dihydroxy-5-methoxyanthraquinone there is utilized 1,4-dihydroxy-5-acetoxyanthraquinone or 5-benzoyloxyanthraquinone, there is obtained the corresponding 5-acetoxyquinizarinquinone or 5-benzoyloxyquinizarinquinone.

EXAMPLE V

Regioisomeric mixture of 1- and 4-methyl ethers of 6a,7,10,10a tetrahydro-1,9- and 4,9-dihydroxy-5,6,11,12-naphthacenetetraone 9-acetate (IV)

5-Methoxyquinizarinquinone (III) (0.3 g, 1.12 mmole) and 2-acetoxy-1,3-butadiene (2.4 g, 21.4 mmole) were stirred in a mixed solvent of xylene (10 ml) and acetic acid (20 ml) at room temperature for 4 days. A yellow solid precipitate separated and was washed well with water. After drying under reduced pressure and filtration through silica gel to remove polymers, a yellow solid comprising the regioisomeric mixture of 1- and 4-methyl esters of 6a,7,10,10a-tetrahydro-1,9- and 4,9-dihydroxy-5,6,11,12-naphthacenetetraone 9-acetate (IV) was obtained (0.3 g, 71% yield). m.p. 165°–9° C.; IR (CDCl$_3$), 5.71, 5.83, 6.01$\mu$; NMR (CDCl$_3$) $\delta$, 7.85–7.32 (m, 3H), 5.50 (m, 1H), 4.05 (s, 3H), 3.80–3.45 (m, 2H), 2.70–2.35 (m, 4H), 2.20 (s, 3H).

In accordance with the above procedures, but where in place of 2-acetoxy-1,3-butadiene there is utilized 2-propionoxy- or 2-benzoyloxy-1,3-butadiene, there is obtained the corresponding 9-propionate, or 9-benzoate respectively.

Similarly, but where in place of 5-methoxyquinizarinquinone, there is utilized 5-benzoxyquinizarinquinone, there is obtained a regioisomeric mixture of the analogues 1-benzyl and 4-benzyl ethers.

Similarly, but where in place of 5-methoxyquinizarinquinone, there is utilized 5-acetoxyquinizarinquinone or 5-benzoyloxyquinizarinquinone, there is obtained a regioisomeric mixture of 6a,7,10-tetrahydro-1,9- and 4,9-dihydroxy-5,6,11,12-naphthacenetetraone-1,9-diacetate and 4,9-diacetate or 9-acetate 1-benzoate and 9-acetate 4-benzoate respectively.

Similarly, to the principal procedure, but where in place of 5-methoxyquinizarinquinone, there is utilized 5-hydroxyquinizarinquinone, there is obtained the mixture of regioisomers of 6a,7,10,10a-tetrahydro-1,9- and 4,9-dihydroxy-5,6,11,12-naphthacenetetraone 9-esters.

EXAMPLE VI

Regioisomeric mixture of 1-methyl and 4-methyl ethers of 7,10-dihydro-1,6,9,11- and 4,6,9,11-tetrahydroxy-5,12-naphthacenedione 9-acetate (V)

A regioisomeric mixture of 1- and 4-methyl ethers of 6a,7,10,10a-tetrahydro-1,9- and 4,9-dihydroxy-5,6,11,12-naphthacenetetraone 9-acetate (IV) (0.38g, 1 mmole) was dissolved in 10 ml. glacial acetic acid at 130°–140°. To this solution was added anhydrous sodium acetate (0.164 g, 2.0 mmole) in portions. After addition, the mixture was heated for an extra 2 minutes and cooled to room temperature. Sufficient water was added to precipitate the product. The precipitate was washed well with water and dried under reduced pressure to give an isomeric mixture of 1-methyl and 4-methyl ether of 7,10-dihydro-1,6,9,11- and 4,6,9,11-tetrahydroxy-5,12-naphthacenedione-9-acetate (V) as a red solid (0.37 g, 100% yield). m.p. 222°-6° C. IR (CDCl$_3$), 5.70, 6.18μ; NMR (CDCl$_3$) δ, 13.80 (d, 1H), 13.40 (d, 1H), 8.04-7.28 (m, 3H), 5.60 (m, 1H), 4.04 (s, 3H), 3.50 (m, 4H), 2.20 (s, 3H).

In accordance with the above procedure, but starting with any of the compounds prepared in accordance with Example V, there are obtained the corresponding regioisomeric mixtures of 7,10-dihydro-1,6,9,11- and 4,6,9,11-tetrahydroxy-5,12-naphthacenedione 9-ester derivatives.

EXAMPLE VII

Regioisomeric mixture of 1-methyl and 4-methyl ethers of 7,10-dihydro-1,6,11- and 4,6,11-trihydroxy-5,9,12(8H)-naphthacenetrione (VI)

The red enolacetates (V) (33.8 mg, 0.09 mmole) were suspended in ethanol (5 ml). The suspension was degassed and flushed with nitrogen. 6N hydrochloric acid (0.1 ml) was added to the mixture which was again degassed and flushed with nitrogen. The mixture was stirred at 80°-85° for 6 hours, cooled to room temperature and diluted with water (20 ml). The mixture was extracted with chloroform (3 × 15 ml) and the chloroform extract was washed once with water (20 ml) and dried over anhydrous sodium sulfate. The solvent was stripped off under reduced pressure to give a dark red residue (31 mg). The residue was chromatographed on silica prep plates (eluting with 5% hexane in chloroform) to give a regioisomeric mixture of 1-methyl and 4-methyl ethers of 7,10-dihydro-1,6,11- and 4,6,11-trihydroxy-5,9,12(8H)-naphthacenetrione (VI), as a dark red solid (25.2 mg, 84% yield). m.p. 230°-234° C. (decomp.); IR (CDCl$_3$), 5.80, 6.18μ; NMR (CDCl$_3$) δ, 13.81, 13.30 (singlets, two phenolic protons of the 4-methoxy isomer), 13.70, 13.41 (singlets, two phenolic protons of the 1-methoxy isomer), 8.00-7.20 (m, 3H), 4.04 (s, 3H), 3.60 (d, 2H), 3.20 (m, 2H), 2.64 (m, 2H).

In accordance with the above procedure but where in place of the 9-acetate there is used the 9-benzoate, the same product is obtained.

Similarly, where the mixture of 1-benzyl and 4-benzyl ether is used in place of the corresponding 1-methyl and 4-methyl esters, the corresponding 1-benzyl and 4-benzyl ether mixture is obtained.

In accordance with the above procedure but starting with the regioisomeric mixtures of 7,10-dihydro-1,6,9,11 and 4,6,9,11-tetrahydroxy-5,12-naphthacenedione 9-acetate or 9-benzoate, the corresponding mixture of 7,10-dihydro-1,6,11- and 4,6,11-trihydroxy-5,9,12-(8H)-naphthacenetriones are obtained.

If in accordance with the above procedure, there is utilized the mixture of regioisomers of 6a,7,10,10a-tetrahydro-1,9- and 4,9-dihydroxy-5,6,11,12-naphthacenetetraone 9-esters or the corresponding ethers themselves produced in accordance with Example V, the intermediate step of Example VI may be omitted to yield the foregoing products directly.

EXAMPLE VIII

4-Methyl ether of 7,10-dihydro-4,6,11-trihydroxy-5,9,12(8H)-naphthacenetrione (VII)

The mixture of isomers produced in accordance with the principal embodiment of Example VII, (50:50) was heated in ethanol to boiling and filtered. The residue was again heated in ethanol to boiling and filtered. The NMR of the second residue showed a better than 90% pure 4-methyl ether (VII). m.p. 242°-245° C. (decomp.). Calcd. = C, 67.46; H, 4.14. Found = C, 66.97; H, 4.31.

In accordance with the foregoing procedure similar treatment of the other regioisomers produced in accordance with Example VII provides a means of separating said regioisomers into the corresponding 1- and 4-isomeric components.

EXAMPLE IX

4-Methyl ether of 9-ethynyl-7,10-dihydro-4,6,9,11-tetrahydroxy-5,12(8H)naphthacenedione (VIII)

Acetylene, purified by passing it first through a column of alumina, then through concentrated sulfuric acid, was bubbled rapidly through freshly distilled tetrahydrofuran (50 ml) under nitrogen for 1 hour. Ethylmagnesium bromide (4 ml, 3.15 M in ether, 12.6 mmole) was added in portions. When the frothing subsides, portionwise addition of the ethylmagnesium bromide solution was continued until the total solution had been added. The passage of methylene was stopped and 1 methyl ether of 7,10-dihydro-4,6,11-trihydroxy-5,9,12(8H)naphthadenedione (VII) (40 mg, 0.12 mmole) in dry tetrahydrofuran (50 ml) was added dropwise. After addition was completed, the mixture was stirred at room temperature under dry nitrogen overnight. The dark blue solution was added carefully to cooled saturated aqueous ammonium chloride (200 ml) and then aqueous hase extracted with ethyl acetate (2 × 50 ml). The ethyl acetate extracts were combined with tetrahydrofuran solution and washed once with saturated aqueous sodium chloride, then water, dried over anhydrous sodium sulfate and the solvent removed to give a dark residue. The residue was chromatographed on silica prep plates, elution with 3% methanol/methylene chloride yielded 4-methyl ether of 9-ethynyl-7,10-dihydro-4,6,9,11-tetrahydroxy-5,12(8H)-naphthacenedione (VIII) (21.9 mg, 50% yield). IR (CDCl$_3$), 2.77, 3.04, 6.19μ; NMR (CDCl$_3$) δ, 13.88 (s, 1H), 13.48 (s, 1H), 8.23-7.20 (m, 3H), 4.07-4.01 (d, 3H), 3.20-2.90 (m, 4H), 2.48 (d, 1H), 2.10 (m, 3H; OH and CH$_2$); mass spectrum, m/e 364 (M+), 346.

In accordance with the above procedure but where in place of the 4-methyl ether there is utilized the corresponding 4-hydroxy compound itself or the 4-benzyl ether, there is obtained the corresponding 9-ethynyl-7,10-dihydro-4,6,9,11-tetrahydroxy-5,12(8H)-naphthacenedione or the 4-benzylether thereof.

In accordance with the foregoing procedures but where there is used as starting material any of the 1- and 4-regioisomeric mixtures prepared in accordance with Example VII, there are obtained the corresponding 1- and 4-regioisomeric mixtures of the appropriate 9-ethynyl carbinols.

EXAMPLE X (±)-7-Deoxydaunomycinone (IX)

To a warm vigorously stirred solution of yellow mercuric oxide (78 mg) in water (3 ml) and concentrated sulfuric acid (0.5 ml) was added quickly to a solution of 4-methyl ether of 9-ethynyl-7,10-dihydro-4,6,9,11-tetrahydroxy-5,12(8H)naphthacenedione (VIII) (26 mg, 0.07 mmole) in chloroform (5 ml). The mixture was then heated at 70°–80° for 4 hours, cooled to room temperature, poured into water (20 ml) and extracted with chloroform (2 × 15 ml). The organic extracts were washed in brine, then water, then dried over anhydrous sodium sulfate. The residue was chromatographed on silica prep plates to give a racemic mixture of (±)-7-deoxydaunomycinone (IX) (10.9 mg, 40% yield). NMR(CDCl$_3$) δ, 13.94 (d, 1H), 13.54 (s, 1H), 8.04–7.28 (m, 3H), 4.03 (s, 3H), 2.98 (m, 4H), 1.92 (m, 2H); Mass spectrum m/e 382 (M+), 364, 339, 321. The spectroscopic and chromatographic properties of this material were identical with 7-deoxydaunomycinone from natural (+)-daunomycinone.

In accordance with the above procedure but where in place of the 4-methyl ether, the 9-ethynyl-7,10-dihydro-4,6,9,11-tetrahydroxy-5,12(8H)naphthacenedione itself is utilized, there is obtained (±)-7-deoxycarminomycinone, r$_f$ (in 3% MeOH—CH$_2$Cl$_2$) = 0.44, relative to daunomycinone (r$_f$ = 0.14).

Similarly, where, in place of the 4-methyl ether there is used the 4-benzyl ether, there is obtained (±)-7-deoxycarminomycinone 4-benzylether.

Further, in accordance with the above procedure where any of the 1- and 4-regioisomeric mixtures of 9-ethynyl carbinols prepared in accordance with Example IX, are used as the starting material, there are obtained the corresponding 1- and 4-regioisomeric mixtures of the appropriate 9-acetal carbinols.

EXAMPLE XI

Regioisomeric mixture of 1- and 4-methyl ethers of 9-acetyl-7,10-dihydro-1,6,9,11- and 4,6,9,11-tetrahydroxy-5,12(8H)-naphthacenedione 9-acetate Regioisomeric mixture of 1- and 4-methyl ethers of 9-ethinyl-7,10-dihydro-1,6,9,11- and 4,6,9,11-tetrahydroxy-5,12(8H)-naphthacenedione (15 mg, 0.04 mmole) and mercuric acetate (75 mg, 0.24 mmole) were suspended in ethyl acetate (10 ml) and the mixture stirred at room temperature overnight. Hydrogen sulfide gas was bubbled through until no more black precipitate was formed. The reaction mixture was filtered through celite and the filtrate evaporated to dryness. The residue was chromatographed on silica prep plates eluted with 10% hexane/chloroform to give an regioisomeric mixture of 1- and 4-methyl ether of 9-acetyl-7,10-dihydro-1,6,9,11- and 4,6,9,11-tetrahydroxy-5,12(8H)-naphthacenedione 9-acetate (4.2 mg, 25% yield). IR (CDCl$_3$), 5.75, 5.82, 6.19μ; NMR (CDCl$_3$) δ, 13.92 (s, 1H), 13.52 (s, 1H), 8.04–7.28 (m, 3H), 4.04 (s, 3H), 3.26–2.90 (m, 4H), 2.40–2.20 (m, 2H), 2.22 (s, 3H), 2.04 (s, 3H); MS, m/e, 424 (M+, 7%), 434 (3%), 374 (39%), 364 (100%).

In accordance with the above procedure but where in place of the mixture of 1- and 4-methyl ethers, there are utilized the corresponding 1- and 4-benzyl ethers, there is obtained the corresponding mixture of the appropriate 9-acetyl acetate. When however, the mixture corresponding to 1- and 4-hydroxy compounds is reacted according to the above procedure there is obtained directly a mixture of the 1-hydroxy isomer of (+)-7-deoxydaunomycinone and (+)-7-deoxycarminomycinone, respectively in 73% total yield.

In accordance with the above procedures, but where in place of the regioisomeric mixtures there is utilized the appropriate 4-ether compound per se produced in accordance with Example IX, there is obtained the corresponding 9-acetyl acetate.

In accordance with all of the foregoing procedures but where in place of mercuric acetate, there is utilized mercuric trifluoroacetate, mercuric propionate, mercuric valerate, or mercuric benzoate, there are obtained from the ethers (VIII) the corresponding 9-acetyl trifluoroacetate, propionates, valerates or benzoates, respectively.

EXAMPLE XII

Regioisomeric mixture of (+)-7-Deoxydaunomycinone and its 1-methoxy isomer

Regioisomeric mixture of 1- and 4-methyl ethers of 9-acetyl-7,10-dihydro-1,6,9,11- and 4,6,9,11-tetrahydroxy-5,12(8H)-naphthacenedione-9-acetate (3 mg, 0.07 mmole) was dissolved in ethanol (5 ml) and water (1 ml). The solution was degassed and flushed with nitrogen 3 times. To the resulting mixture was added 0.05N aqueous sodium hydroxide (1 ml) and the resultant solution degassed and flushed with nitrogen. The mixture became dark blue and was stirred at room temperature for 3 hours. The reaction mixture was poured onto crushed ice (10 g) and 3N aqueous hydrochloric acid and extracted with ethyl acetate (2 × 10 ml). The extract was washed with water and dried over anhydrous sodium sulfate. The solvent stripped off under reduced pressure and the residue chromatographed on silica prep plate, and eluted with 10% hexane/chloroform to give a mixture of (+)-7-deoxydaunomycinone and its 1-methoxy regioisomer (2.7 mg, 100% yield).

In accordance with the foregoing procedures, but starting instead with any of the other b 9-acetyl-9-esters produced in accordance with Example XI, there is produced the corresponding 9-acetyl carbinol.

EXAMPLE XIII

Daunomycinone and epi-daunomycinone (a) Dry nitrogen was bubbled rapidly through a solution of (+)-7-deoxydaunomycinone (7.1 mg) in carbon tetrachloride (50 ml). The solution was irradiated with a GE-sunlamp while a solution of bromine in carbon tetrachloride (2 ml, 0.1 M) was added very slowly with stirring. The reaction is periodically monitored using h.p.l.c. (three 2' × ⅛" Corasil columns eluted with chloroform in a Waters h.p.l.c. unit, flow rate 0.6 ml/min.). Bromine addition and irradiation are continued for 2–3 hours until h.p.l.c. shows disappearance of over 80% of the starting material. The solution is concentrated and the residue was taken up in chloroform.

(b) An 0.5 mm silica gel tlc plate (F-254, EM Lab #5769-9H) was pretreated by elution with 3% methanol in methylene chloride and allowed to air dry in a hood. The chloroform solution was then carefully applied and the plate eluted as usual with 3% methanol in methylene chloride. Bands corresponding to (+)-daunomycinone (R$_f$ = 0.27), (+)-7-epidaunomycinone (R$_f$ = 0.25) and a little starting material (R$_f$ = 0.5) were separately isolated, extracted with 10% methanol in methylene chloride and concentrated. The above R$_f$ values refer to hydrated plates. Each residue was taken up in chloroform and filtered through a glass fiber plug and concentrated.

From this procedure there are obtained the following products:

(+)-daunomycinone (1.3 mg), (+)-7-epidaunomycinone (2.1 mg) and (+)-7-deoxydaunomycinone (1.0 mg. starting material).

In accordance with the foregoing procedure, but where in place of (+)-7-deoxydaunomycinone there is utilized (+)-7-deoxycarminomycinone and other 4-ethers of (+)-7-deoxycarminomycinone, there is obtained (+)-carminomycinone, (+)-7-epicarminomycinone, and (+)-7-deoxycarminomycinone(starting material), all of which are separable from each other, and the corresponding 4-ethers thereof when the appropriate (+)-7-deoxy-4-ethers are used as starting materials.

EXAMPLE XIV

Epimerization of (+)-7-epidaunomycinone to (+)-daunomycinone

The (+)-7-epidaunomycinone (2.4 mg) above was taken up in trifluoroacetic acid (1.5 ml) and the solution allowed to stand 2 hours at room temperature. The reaction was poured into water (5 ml), extracted with chloroform and the chloroform washed well with water, then dried over sodium sulfate. Chromatography as described above (3% methanol/methylene chloride) gave (+)-daunomycinone as the major product (1.8 mg) accompanied by traces of 7-epidaunymycinone, a non-polar purple band, and 2 less polar orange bands. The identity of this daunomycinone was confirmed by ms and h.p.l.c. analysis (same system as before, flow rate 1.0 ml chloroform 3/min.) by comparison with (+)-daunomycinone derived from natural daunomycin.

In accordance with the foregoing procedure, but starting with (+)-7-epicarminomycinone or any of the other (+)-7-epicarminomycinone 4-ethers, there are obtained the corresponding (+)-carminomycinone and (+)-7-carminomycinone 4-ethers.

EXAMPLE XV

Resolution of (+)-daunomycinone

Recamic daunomycinone (10 mg) is taken up in dry benzene (2 ml) and dry pyridine (3 drops) are added, followed by freshly prepared 1-menthoxyacetyl chloride (30 mg). The reaction mixture is refluxed for 30 minutes, allowed to cool, then poured into water and extracted with chloroform. The chloroform extracts are combined, washed with 5% aqueous oxalic acid, followed by water and brine. The chloroform are dried over anhydrous sodium sulfate, concentrated at reduced pressure, and the residue applied to a preparative thin-layer plate of silica gel. Elution with 3% methanol in methylene chloride (v/v) produces an orange band between $R_f = 0.3$ and 0.38. The segment at $R_f = 0.33$ is carefully removed and extracted with 10% methanol in methylene chloride, then the eluate concentrated and rechromatographed in the identical manner. There is thus obtained the 1-menthoxyacetyl ester (at C-7 OH) of (+)-daunomycinone.

The 1-menthoxyacetyl ester is dissolved in ethanol (2 ml), the solution degassed and flushed with nitrogen three times, and several drops of 2M sodium hydroxide are added. The resulting solution is again degassed and flushed with nitrogen, then stirred at 25° for 3 hours. The mixture is poured onto ice and dilute aqueous oxalic acid, extracted with chloroform, the extracts washed and dried over anhydrous sodium sulfate. After solvent removal, the residue is chromatographed on silica and the (+)-daunomycinone isolated.

EXAMPLE XVI

4-O-Demethylation of daunomycinone derivatives (a) Natural daunomycinone (14.7 mg) was taken up in anhydrous benzene (100 ml). Sea sand (1 g) was added and the mixture was stirred until all the daunomycinone went into solution. The reaction was stirred under nitrogen and anhydrous aluminum chloride (0.22 g) was added. The reaction gradually turned purple; stirring was continued at room temperature overnight. The reaction was worked up by pouring in aqueous oxalic acid (25 ml., 25%) and the layers mixed thoroughly until the color was discharged. The aqueous phase was extracted once with chloroform (10 ml) and the chloroform added to the benzene. The combined organic phases were washed once with water, dried over anhydrous sodium sulfate and concentrated to give (+)-carminomycinone, $R_f = 0.16$ (on silica gel, 3% methanol in methylene chloride, v/v). The mass spectrum showed 384 (M+, 45%), 366 (7%), 348 (100%), 341 (3%), 333 (21%), 323 (67%), 305 (19%), 295 (39%, 277 (16%), 249 (8%). The NMR (CDCl$_3$) taken using Fourier-transform spectroscopy gave δ 13.47, 12.96, 12.17 (s, 1H ea); 7.14–7.25 (m, 3H), 2.43 (s, 3H), 2.27 (m, 2H); the vv spectrum showed maxma at 527, 512, 492, 480 and 466 nm.

Application of the above demethylation to racemic daunomycinone proceeds in the identical manner to yield (+)-carminomycinone.

(b) Treatment of 11.5 mg of 7-deoxydaunymycinone in dry benzene (45 ml) with sea sand (0.5 g) and anhydrous aluminum chloride (0.1 g) under dry nitrogen overnight, as in the Example above, followed by work-up as described above gave 7-deoxycarminomycinone (10.9 mg), $R_f = 0.44$ (3% methanol in methylene chloride v/v), MS 368 (27%), 327 (33%), 326 (21%), 325 (100%), 307 (20%), NMR (CDCl$_3$) δ 13.62, 12.81, 12.28 (s, 1H ea). 7.84–7.25 (m, 3H), 2.38 (s, 3H).

(c) A suspension of the 4-methyl ether of 7,10-dihydro-4,6,11-trihydroxy-5,9,12(8H)-naphthacenetrione (VII, R$_1$ = CH$_3$) (20 mg., 0.06 mmole) in anhydrous methylene chloride (ml ml) was stirred at room temperature under dry nitrogen with an excess of anhydrous aluminum chloride (133 mg, 1 mmole). After 16 hours, the reaction was quenched with 5% aqueous oxalic acid as in the above procedure and the demethylation product isolated by chloroform (3 × 20 ml) extraction, water wash (2 × 20 ml), drying over sodium sulfate and solvent removal. There was obtained 17 mg. of the red trihydroxy compound, MS 324 (M+), NMR (CDCl$_3$)δ 13.64, 12.74, 12.22 (s, 1H ea), 7.88–7.20 (m, 3H), 3.60 (s, 2H), 3.21 (t, 2H), 2.62 (t, 2H).

EXAMPLE XVII

Reference chromatographic values for synthetic materials

Using 250μ thickness precoated silica gel GF plates from Araltech (Uniplates) and an eluting solvent of 3% methanol in methylene chloride (V/V), the following R$_f$ values were reproducibly observed (+0.01):

(+)-daunomycinone — 0.14
(+)-7-deoxydaunomycinone — 0.26
(+)-7-epidaunomycinone — 0.08
(+)-carminomycinone — 0.16
(+)-7-epicarminomycinone — 0.13
(+)-7-deoxycarminomycinone — 0.44.

We claim:

1. A derivative of 5-hydroxy quinizarinquinone having the formula

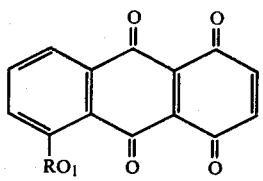

wherein $R_1$ is a lower alkyl or lower alkanoyl of 1–5 carbon atoms; phenyl, phenyl carbonyl, substituted phenyl-lower alkyl, or lower alkanoyl, wherein the substituent groups are lower alkyl, lower alkoxy, each containing 1–5 carbon atoms, or halo; and the lower alkyl, lower alkanoyl moieties contain 1–5 carbon atoms.

2. Esters of claim 1 wherein $R_1$ is lower alkanoyl of 1–5 carbon atoms or phenyl-lower alkanoyl of 1–5 carbon atoms in the alkanoyl moiety.

3. Esters of claim 2 wherein $R_1$ is acetyl or benzoyl.

4. Ethers of claim 1 having the formula

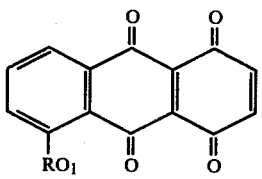

wherein $R_1$ is a lower alkyl of 1–5 carbon atoms; phenyl- or substituted phenyl-lower alkyl wherein the substituent groups are lower alkyl, lower alkoxy, each containing 1–5 carbon atoms, or halo; and lower alkyl contains 1–5 carbon atoms.

5. Ethers of claim 4 wherein $R_1$ is lower alkyl of 1–5 carbon atoms or phenyl lower alkyl containing 1–5 carbon atoms in the alkyl moiety.

6. Ethers of claim 2 wherein $R_1$ is methyl or benzyl.

7. Process for the preparation of a compound of claim 1 which comprises oxidizing a derivative of 1,4,5-hydroxy anthraquinone of the formula

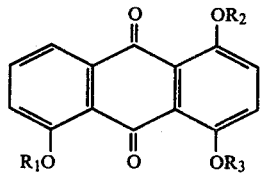

wherein $R_1$ has the same definition of claim 1, $R_2$ and $R_3$ are hydrogen, lower alkyl, phenyl lower alkyl, substituted phenyl lower alkyl wherein the substituents are lower alkyl, lower alkoxy or halo, wherein the moiety lower alk contains 1–5 carbon atoms and $R_1$, $R_2$ and $R_3$ may be the same or different.

8. A process of claim 7 wherein $R_1 = R_2 = R_3$.

9. A process of claim 8 wherein $R_1 = R_2 = R_3 =$ lower alkyl.

10. A process of claim 9 wherein $R_1 = R_2 = R_3 =$ methyl and the oxidizing agent is argentic oxide in the presence of an acid.

11. A process of claim 10 wherein the oxidizing agent is argentic oxide in the presence of nitric acid.

12. A process of claim 7 wherein $R_2 = R_3 =$ hydrogen and the oxidizing agent is lead tetraacetate.

13. A mixture of the 1- and 4- regioisomers of the formula

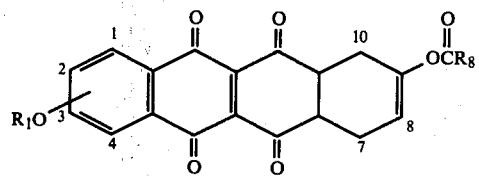

wherein $R_1$ is as defined in claim 1, or hydrogen, $R_8$ has the definition of $R_1$ as defined in claim 1, and $R_1$ and $R_8$ may be the same or different.

14. The mixture of claim 13 wherein $R_1$ is hydrogen or lower alkyl and wherein $R_8 =$ lower alkyl.

15. The mixture of claim 13 wherein $R_1$ is methyl or hydrogen and $R_8$ is methyl, phenyl or hydrogen.

16. The process of preparing a mixture of claim 13 which comprises subjecting a compound of the formula

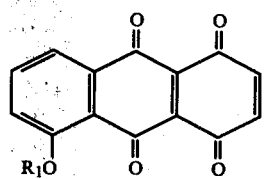

to a Diels-Alder condensation with a compound of the formula

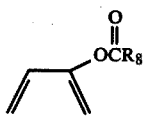

wherein $R_1$ and $R_8$ are as defined in claim 13.

17. A compound of the formula

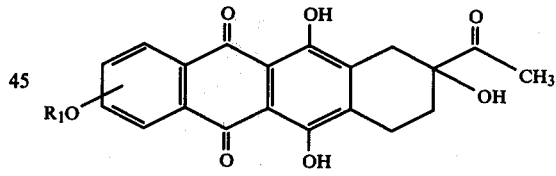

wherein $R_1$ is as defined in claim 4 and the group $R_1O$ is attached to the 1- or the 4-position of the nucleus.

18. A compound of claim 17 wherein the group $R_1O$- is in the 4-position of the nucleus.

19. The process of converting a compound of the formula:

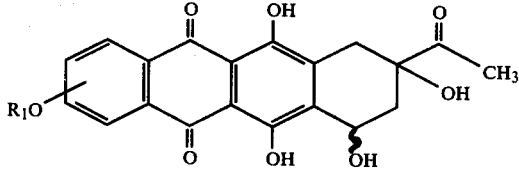

wherein $R_1O$- represents an ether moiety as defined in claim 4 to the corresponding material wherein $R_1$ is hydrogen which comprises reacting the starting material with aluminum chloride.

* * * * *